United States Patent [19]

Murali

[11] Patent Number: 5,736,145
[45] Date of Patent: Apr. 7, 1998

[54] PROCESS FOR PREPARING PURIFIED AZADIRACHTIN IN POWDER FORM FROM NEEM SEEDS AND STORAGE STABLE AQUEOUS COMPOSITION CONTAINING AZADIRACHTIN

[75] Inventor: P. M. Murali, Tamil Nadu, India

[73] Assignee: Dalmia Centre for Biotechnology, Tamil Nadu, India

[21] Appl. No.: 683,506

[22] Filed: Jul. 17, 1996

[30] Foreign Application Priority Data

Jul. 17, 1995 [IN] India ........................ 898/MAS/95

[51] Int. Cl.$^6$ ........................ A01N 65/00; A01N 43/16
[52] U.S. Cl. ........................ 424/195.1; 514/453; 424/405
[58] Field of Search ........................ 424/195.1, 405; 514/453

[56] References Cited

U.S. PATENT DOCUMENTS

| | | | |
|---|---|---|---|
| H1541 | 6/1996 | Holla | 424/195.1 |
| 4,556,562 | 12/1985 | Larson | 424/195.1 |
| 4,943,434 | 7/1990 | Lidert | 424/195.1 |
| 4,946,681 | 8/1990 | Walter | 424/195.1 |
| 5,124,349 | 6/1992 | Carter et al. | 514/453 |
| 5,229,007 | 7/1993 | Ellenberger et al. | 210/690 |
| 5,281,618 | 1/1994 | Walter | 514/453 |
| 5,298,251 | 3/1994 | Locke et al. | 424/405 |
| 5,299,007 | 3/1994 | Saeger et al. | 348/563 |
| 5,352,697 | 10/1994 | Butler et al. | 514/468 |
| 5,372,817 | 12/1994 | Locke et al. | 424/405 |
| 5,391,779 | 2/1995 | Lidert | 514/453 |
| 5,420,318 | 5/1995 | Lidert et al. | 554/193 |

FOREIGN PATENT DOCUMENTS

| | | |
|---|---|---|
| 153415 | 12/1979 | India . |
| 173998 | 6/1990 | India . |
| 173989 | 11/1990 | India . |
| 172150 | 4/1993 | India . |
| 173327 | 2/1994 | India . |
| 173327 | 4/1994 | India . |
| 173328 | 4/1994 | India . |
| 173449 | 5/1994 | India . |
| 173996 | 8/1994 | India . |
| 173997 | 8/1994 | India . |

OTHER PUBLICATIONS

Pavia et al. Intro. to Organic Laboratory Techniques, 2nd Ed, pp. 500–501, 1982.

*Primary Examiner*—Leon B. Lankford, Jr.
*Assistant Examiner*—Christopher R. Tate
*Attorney, Agent, or Firm*—Lowe, Price, LeBlanc & Becker

[57] ABSTRACT

A storage stable formulation of Azadirachtin, a process for its preparation, and a process of preparing purified Azadirachtin powder enriched in Azadirachtin A from neem seeds is disclosed.

17 Claims, No Drawings

PROCESS FOR PREPARING PURIFIED AZADIRACHTIN IN POWDER FORM FROM NEEM SEEDS AND STORAGE STABLE AQUEOUS COMPOSITION CONTAINING AZADIRACHTIN

BACKGROUND

Several powerful and effective synthetic insecticides have been used to protect food and fibre crops varied success for many years now. More recently, there has been a great deal of controversy about the effect insecticides on the environment. Some of these insecticides that have been extensive use have been banned. It is likely that other alternatives will be banned in the near future. Due to lack of other alternatives some use in spite of their harmful effects to the environment.

As a result, a search has been going on for "botanical pesticides" that are soft and environmental friendly. These are compounds that would deter insects or other pests but would have minimal harmful or no effect on the environment and in particular to humankind who are at most times at the end of the food chain and bio-accumulation.

Presently, an agent known to protect crop from pests is Azadirachtin that is a natural product found in the seeds of the neem tree (*Azadirachtin indica A. Juss*). The neem tree is in great abundance in India and also distributed in other countries like Pakistan, Bangladesh, Thailand, Malaysia and Africa. Azadirachtin has gained a lot of importance all over the world as the most environmentally safe pesticide.

Azadirachtin and more particularly Azadirachtin A, is extracted from neem seeds and found to have growth regulation and anti-feedant properties that deters insects from feeding on plants. It is readily applied by a foliar spray to the crops.

The commercial uses of Azadirachtin formulations have been based on its stability which is dependent on the method of purification. Various methods of extracting & formulating Azadirachtin, a known agent from seeds and kernels have been described in U.S. Pat. Nos. 4,556,562, 5,391,779, 5,372,817, 5,352,677, 5,298,251, 5,281,618, 5,229,007 and 5,124,349.

These processes for obtaining crude neem extracts without adequate importance to Azadirachtin A enrichment typically comprised the steps of:

a) extracting the ground seed with a polar organic solvent such as ethanol followed by centrifugation and/or filtration, b) removing the solvent from the filtrate by evaporation under reduced pressure to yield a dry extract, c) dissolving the dry extract in a mixture of a water-immiscible polar organic solvent, such as ethyl-acetate, and aqueous saturated sodium chloride solution and d) separating the organic layer, drying and evaporating the solvent to yield the semi-pure extract.

Such prior processes resulted in extracts containing a significant portion of hydrophobic organic impurities and no more than 10% Azadirachtin and without high enrichment for Azadirachtin A. A few higher purity preparations have been described that are mostly uneconomical with non-scaleable chromatographic steps subsequent to those steps described above.

Not withstanding the above advance, there remains a need for an economical, stable composition effective to control pests, preferably a composition which is also free of aflatoxins.

However, purification has not adequately focused on the enrichment of Azadirachtin A in these patents, that is considered to possess the botanical property against insects.

It is therefore the object of this invention to prepare enriched Azadirachtin A in a stable and purified form while purifying Azadirachtin.

To achieve the said objective this invention provides a process of preparing purified Azadirachtin powder enriched in Azadirachtin A from neem seeds comprising:

Decortication of neem seeds followed by pelleting to obtain neem kernels pellets, adding ketone and water solvent in the ratio 88–92:8–12 to the said neem kernels for extracting 80% enriched Azadirachtin without oozing, i.e., leakage or abstraction of neem oil from the neem seeds involving multiple passes of the said solvent through the said kernel pellets at 45–60 deg. C. and filtering, treating the extract enriched Azadirachtin with dichloromethane at least twice to extract 50,000 to 100,000 ppm Azadirachtin, separating ketone by centrifugation and evaporating dichloromethane under vacuum to get purified Azadirachtin with enriched Azadirachtin A.

removal of trace oil and soluble hydrophobic impurities with hexane.

removing the moisture from the said purified Azadirachtin obtained from step 4 by using an anhydrous salt to obtain pure Azadirachtin powder enriched in Azadirachtin A.

The ketone used in the process is preferably acetone having high dielectric constant.

The anhydrous salt used in the process is preferably anhydrous sodium sulphate.

The acetone:water ratio used for extracting enriched 80% Azadirachtin without oozing oil is preferably 90:10 and the extraction is carded out at 60 deg. C. and is further enriched by passing it through dichloro-methane preferably 3 times or even more.

Removal of trace oil and soluble hydrophobic impurities with hexane.

This invention further relates to a process of preparing storage stable aqueous Azadirachtin enriched in Azadirachtin A containing composition which comprises:

obtaining 50,000–70,000 ppm Azadirachtin as described above, diluting the said Azadirachtin with ethanol::water 100–70:0–30 to 2000–4000 ppm and forming an emulsion with non ionic and non toxic emulsifying agent in an amount ranging from 0.2 to 30% and neem oil 20–50%, adjusting the pH of diluted Azadirachtin to 3.5 to 6.0 by adding alkali solution, adding 1–2.5% sunscreen like p.aminobenzoic acid or its esters after pH adjustment for stabilizing the composition.

Preferred non ionic and non toxic emulsifying agents used in the process are sorbitan esters, ethoxylated and propoxylated mono or diglycerides, acetylated mono or diglycerides, lactylated mono or diglycerides citric acid esters of mono. or diglycerides, sugar esters, polysorbates and polyglycerol esters. Preferred emulsifier is polyoxyethylene sorbitan monolaurate which is sold under the name Tween 20 (R).

The alkali solution used in the process is $NH_4OH$ and the emulsifying agent preferably used is 15–25% of the composition.

An oleic acid 1–10% of the composition is added to create microemulsion for stability with a good bio-efficacy.

This invention further relates to storage stable aqueous Azadirachtin containing composition comprising 2000–4000 ppm Azadirachtin having a pH ranging from 3.5 to 6.0, 20–50% neem oil, 0:2–30% non ionic, non toxic emulsifying agent, 1–2.5% sunscreen comprising para-aminobenzoic acid or its esters and an oleic acid 1–10%.

DETAILED DESCRIPTION

The step of forming neem kernel pellets involves decortication of neem seeds either manually or using a groundnut, i.e., peanut decorticator and pelleting with a pelleting machine.

The extraction of 80% enriched Azadirachtin without abstraction of oil therefrom is carried out using acetone and water (hereinafter referred to as "extracting agent") in the ratio 90:10 at 60 deg. C. by involving multiple passes of the said acetone water solvent through the pelleted neem kernels.

This involves, for example, passing a batch of extracting agent through the neem kernels to remove Azadirachtin (without deliberately abstracting neem oil) and recovering it and then passing another batch of extracting agent through the kernels again and continuing this process until a total of 3 to 5 passes and pooled. The extract is filtered using an ordinary filter paper to remove clay sand and some scum. The extract is then washed several times with dichloromethane. The dichloromethane extract is pooled and moisture removed with sodium sulphate anhydrous. Dichloromethane is removed, distilled and recovered. Removal of and trace neem oil and soluble hydrophobic impurities is carded out with a wash with hexane. Purified Azadirachtin enriched in Azadirachtin A is struck on the walls of the container which is scrapped and collected. Dichloromethane is used in the process as it is environmentally friendly solvent.

The step of diluting to form an emulsion comprises adding diluent, preferably ethanol:water::100–70:0–30, and emulsifying agent along with oleic acid comprising from about 2,000 to about 4,000 ppm Azadirachtin A usually from about 20% TO ABOUT 25% neem oil. Ethanol:water is preferably in the ratio 70:30.

It is highly preferred to include an emulsifying agent in the composition so that the Azadirachtin and neem oil and any other ingredients are kept uniformly distributed in the composition. The percentage of the composition which is emulsifier normally depends on the emulsifier which is used typically and emulsifying agent that is the active ingredient is used in an amount ranging from about 0.2% to about 25%.

Preferred emulsifying agents are those normally utilized in foods and include sorbitan esters, ethoxylated and propoxylated mono or diglycerides, acetylated mono or diglycerides, lactylated mono or diglycerides citric acid esters of mono or diglycerides, sugar esters, polysorbates and polyglycerol esters. Preferred emulsifier is polyoxyethylene sorbitan monolaurate which is sold under the name Tween 20 (R).

It is preferred to include oleic acid at a level for example of about 1–10% to aid microemulsion preparation and about 1% sunscreen like p.aminobenzoic acid.

The formulation/composition herein contains Azadirachtin A at a level ranging from about 2,500 to about 3,000 and has a pH ranging from about 3.8 to about 4.2 optimally. It contains Azadirachtin A at a level of about 3,000 ppm and has a pH ranging from about 3.84 to about 4.0.

It has been found that the concentration of Azadirachtin A and pH level are both very important in respect to storage stability and that inside the limits recited herein Azadirachtin A levels are substantially maintained up to two years or more.

As previously indicated, it is highly desirable to add off present extracted from the neem seeds in the composition herein. It is noted that the amount of neem oil ranges from about 20% to about 50% of neem seeds.

EXAMPLE 1

3 kg of decorticated kernel collected from Tamil Nadu, India is used in the extraction.

Acetone water in the ratio of 90:10 is used for extracting. The extracts are pooled. A minimum of three extractions is required at elevated temperatures mentioned above with an optimum of 60° C. The first extract is filtered and an equal volume of Dichloromethane is added and extracted. Three extracts of Dichloromethane of the aqueous extract is pooled. Anhydrous sodium sulphate is added and water if any in excess is removed. The Dichloromethane is distilled and recovered. The enriched Azadirachtin A is used further for formulation.

To the extract is added Tween 20 (R) (consisting of water and polyoxyethylene sorbitan monolaurate) to obtain a diluted extract containing 3,000 ppm Azadirachtin and 20% neem oil.

To the resulting emulsion is added ammonia hydroxide to adjust the pH to 4.0.

To this is added 1% p-amino benzoic acid or its esters and 1% oleic acid.

This formulation is an agent against a wide spectrum of pests and is shelf stable for more than 2 years after formulation.

Product containing 3,000 ppm Azadirachtin and having a pH of 4.0 maintained under normal shelf life conditions (without refrigeration or addition of sunscreen) was found to have retained 65% of its potency even two years later.

EXAMPLE II

Processing of neem pellets is carded out as in Example 1 except that separation of extract from the pellets is carried out by centrifuging. The resulting product as in Example 1 is effective against a wide spectrum of insects.

We claim:

1. A process for preparing a substantially purified Azadirachtin A powder, comprising the steps of:
   a) passing at least three batches of an aqueous polar solvent through decorticated and pelleted neem seeds to obtain a solvent extract, wherein neem oil is not oozed from said seeds;
   b) removing Azadirachtin A from said solvent extract with a polar solvent to obtain an Azadirachtin A solution;
   c) removing the polar solvent from the Azadirachtin A solution to obtain a concentrated Azadirachtin A solution;
   d) removing trace oil and hydrophobic impurities from the concentrated Azadirachtin A solution with a non-polar solvent;
   e) removing water from the concentrated Azadirachtin
   f) recovering a substantially purified Azadirachtin A powder.

2. The process of claim 1, further comprising:
   the step of filtering the solvent extract obtained in step a).

3. The process of claim 1, wherein:
   the solvent extract, substantially free of neem oil, is obtained by passing at least two batches of aqueous polar solvent through the decorticated and pelleted neem seeds.

4. The process of claim 1, wherein:

the aqueous polar solvent contains a ketone and water in a ratio of about 88–92:8–12 and is at about 60° C.

5. The process of claim 1, wherein:

the aqueous polar solvent comprises a ketone.

6. The process of claim 5, wherein:

the ketone is acetone having a high dielectric constant.

7. The process of claim 1, wherein:

the Azadirachtin A is removed from said filtered extract by using at least two batches of polar solvent.

8. The process of claim 1, wherein:

the polar solvent in step b) is dichloromethane.

9. The process of claim 1, wherein:

the non-polar solvent used in step e) is hexane.

10. The process of claim 1, wherein:

step e) is performed by the addition of anhydrous sodium sulphate.

11. The process of claim 1, wherein:

the aqueous polar solvent comprises a mixture of acetone and water in the ratio 90:10.

12. A process for preparing a substantially purified Azadirachtin A powder, comprising the steps of:

a) decorticating and pelleting a quantity of neem seeds;

b) passing at least three batches of an aqueous polar solvent through the decorticated and pelleted neem seeds to obtain a solvent extract, wherein neem oil is not oozed from said neem seeds, wherein the aqueous polar solvent contains a ketone and water in a ratio of about 88–92:8–12 and is at about 60° C.;

c) filtering the solvent extract obtained in step a;

d) removing Azadirachtin A from said filtered extract with a polar solvent to obtain an Azadirachtin A solution;

e) removing the polar solvent from the Azadirachtin A solution to obtain a concentrated Azadirachtin A solution;

f) removing trace oil and hydrophobic impurities from the concentrated Azadirachtin A solution with a non-polar solvent;

g) removing water from the concentrated Azadirachtin A solution; and, h) recovering a substantially purified Azadirachtin A powder.

13. The process of claim 12, wherein: the ketone is acetone having a high dielectric constant.

14. The process of claim 12, wherein: the polar solvent in step c) is dichloromethane.

15. The process of claim 12, wherein the non-polar solvent used in step e) is hexane.

16. The process of claim 12, wherein: step g) is performed by the addition of anhydrous sodium sulphate.

17. The process of claim 12, wherein:

the aqueous polar solvent comprises a mixture of acetone and water in the ratio 90:10.

\* \* \* \* \*